United States Patent
Debono et al.

(10) Patent No.: US 8,461,517 B2
(45) Date of Patent: Jun. 11, 2013

(54) AMMONIUM SALTS AS IMS POSITIVE MODE CALIBRANTS/REACTANTS

(75) Inventors: Reno F. Debono, Clinton, NJ (US); Paul Christopher Peter Thomson, Mississauga (CA)

(73) Assignee: Smiths Detection Montreal Inc., Quebec (CA)

( * ) Notice: Subject to any disclaimer, the term of this patent is extended or adjusted under 35 U.S.C. 154(b) by 230 days.

(21) Appl. No.: 13/124,213

(22) PCT Filed: Oct. 26, 2009

(86) PCT No.: PCT/US2009/062010
§ 371 (c)(1),
(2), (4) Date: Jun. 8, 2011

(87) PCT Pub. No.: WO2010/051241
PCT Pub. Date: May 6, 2010

(65) Prior Publication Data
US 2011/0240838 A1    Oct. 6, 2011

Related U.S. Application Data

(60) Provisional application No. 61/193,088, filed on Oct. 27, 2008.

(51) Int. Cl.
*G01D 18/00* (2006.01)
(52) U.S. Cl.
USPC ......... 250/252.1; 250/281; 250/282; 250/283
(58) Field of Classification Search
USPC ....................................... 250/252.1, 281–289
See application file for complete search history.

(56) References Cited

U.S. PATENT DOCUMENTS

| | | | | |
|---|---|---|---|---|
| 6,825,460 B2 * | 11/2004 | Breach et al. | | 250/287 |
| 7,663,099 B2 * | 2/2010 | Reda | | 250/286 |
| 2009/0179145 A1 * | 7/2009 | Crouch et al. | | 250/281 |

FOREIGN PATENT DOCUMENTS

| | | |
|---|---|---|
| DE | 102 12 110 A1 | 9/2003 |
| EP | 0 447 158 A2 | 11/1991 |
| WO | WO 00/79261 A1 | 12/2000 |
| WO | WO 2006/129101 A1 | 12/2006 |
| WO | WO 2007/148045 A1 | 12/2007 |

OTHER PUBLICATIONS

Recent insights into the formation and chemical composition of atmospheric nanoparticles from the Atlanta Aerosol Nucleation and realtime characterization experiment (Atlanta—ANARChE), Smith et al., Aug. 2002. Department of Energy.*
Communication pursuant to Article 947(3) EPC Application No. 09 806 062.7 dated Aug. 21, 2012.
J.N. Smith et al., "Atmospheric Measurements of Sub-20 nm Diameter Particle Chemical Composition by Thermal Desorption Chemical Ionization Mass Spectrometry", Aerosol Science and Technology, 38:100-110, 2004.
International Search Report for PCT/US2009/062010, issued Mar. 29, 2010, 3 pages.

* cited by examiner

*Primary Examiner* — David Porta
*Assistant Examiner* — Taeho Jo
(74) *Attorney, Agent, or Firm* — Foley & Lardner LLP

(57) ABSTRACT

An ion mobility spectrometer includes a permeation tube, ammonium sulfate disposed within the permeation tube in solid form, and a heating device configured to heat the permeation tube so as to create ammonia gas to flow within the permeation tube. When an array of sensors of the IMS is placed in contact with an unknown sample, the ammonia operates as a reactant so as to provide detection signals that are provided to a processor unit of the IMS, so as to identify the unknown sample based on its ion mobility spectrum.

6 Claims, 2 Drawing Sheets ns IMS POSITIVE
MODE CALIBRANTS/REACTANTS

RELATED APPLICATIONS

This application claims priority to U.S. Provisional Patent Application 61/193,088, filed Oct. 27, 2008, the disclosure of which is incorporated in its entirety herein by reference.

FIELD

The field is sensors, including ion mobility spectrometry (IMS) sensors and the like.

Background

Sensor devices having sensor arrays are becoming very useful in today's society, with the threat of chemi and bio-terrorism being more and more prominent. In more detail, chemical and biological warfare pose both physical and psychological threats to military and civilian forces, as well as to civilian populations.

Ion mobility spectrometry can be used to detect a wide variety of chemicals, including trace amounts of explosives and narcotics. Thus, ion mobility spectrometry (IMS) is an attractive tool for detecting illicit or dangerous substances.

Sensor devices are used in security scanning systems, such as in airports and at country borders. At least some known security scanning systems employ IMS to localize and/or identify contraband, such as narcotics and explosives. Many such spectrometers add ammonia gas molecules to a carrier gas to filter a spectrum analyzed by the spectrometer by removing interfering compounds, such as environmental compounds. At least some known spectrometers use ammonia gas generated from the evaporation of liquid anhydrous ammonia. The liquid ammonia must be pressurized to maintain a liquid form at room temperature.

U.S. Patent Publication 2009/0166531 describes the generation of ammonia gas within an IMS via an ammonia compound, whereby the ammonia compound is ammonium carbamate ($NH_4NH_2CO_2$), which is a type of ammonium salt. It describes that ammonium carbamate is advantageous for use in an IMS since it decomposes into ammonia ($NH_4$) and carbon dioxide ($CO_2$) without producing any water vapor, whereby water vapor may degrade the selectivity of IMS systems.

Ammonium carbamate, ammonium carbonate and ammonium bicarbonate are closely related to each other, and have slightly different chemical structures: $(NH_4)_2CO_3$-ammonium carbonate; ($NH_4NH_2CO_2$)-ammonium carbamate; ($NH_4$)$HCO_3$-ammonium bicarbonate. Ammonium carbonate co-exists with ammonium carbamate and ammonium bicarbonate, and each compound can convert from one to another depending on temperature and humidity.

Smiths Detection has been using an ammonium carbonate/carbamate source in products since at least 1994. For example, ammonium carbonate/carbamate has been used in the following Smiths Detection products: Improved Agent Chemical Monitor-D (ICAM-D), Improved Agent Chemical Monitor-APD (ICAM-APD), and APD2000. Also, Smiths Detection has been using ammonia dopant in systems such as, for example, GID 3 ACADA, which is a highly sensitive point atmospheric monitoring product that uses permeation sources with ammonium carbamate provided within thin walled polymer tubes with capped ends, in which the ammonium carbamate decomposes to produce ammonia gas for dopant. Other Smiths Detection products that use ammonia dopant include the LCD product line for portable chemical agent detectors. The LCD products include a doped sieve, in which anhydrous ammonia ($NH_3$) is used to dope the sieve.

SUMMARY

Accordingly, there is a need for a method and apparatus for generating an ammonia gas for an IMS system with improved properties over conventional methods and apparatuses.

In accordance with one aspect, there is provided a calibrant for an ion mobility spectrometer that comprises ammonium sulfate.

In accordance with another aspect, there is provided a method for providing a calibrant for an ion mobility spectrometer, which includes heating in an ion mobility spectrometer a permeation tube containing at least ammonium sulfate in solid form, to release ammonia, and which includes detecting the ammonia.

In accordance with yet another aspect, there is provided a computer readable medium embodying computer program product for providing a calibrant for an ion mobility spectrometer. The computer program product, when executed by a computer or a microprocessor, causes the computer or the microprocessor to perform a step of heating in an ion mobility spectrometer a permeation tube containing at least ammonium sulfate in solid form, to release ammonia, and to perform the step of detecting the ammonia.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments and, together with the description, serve to explain the principles of the invention.

DETAILED DESCRIPTION

Figure 1:
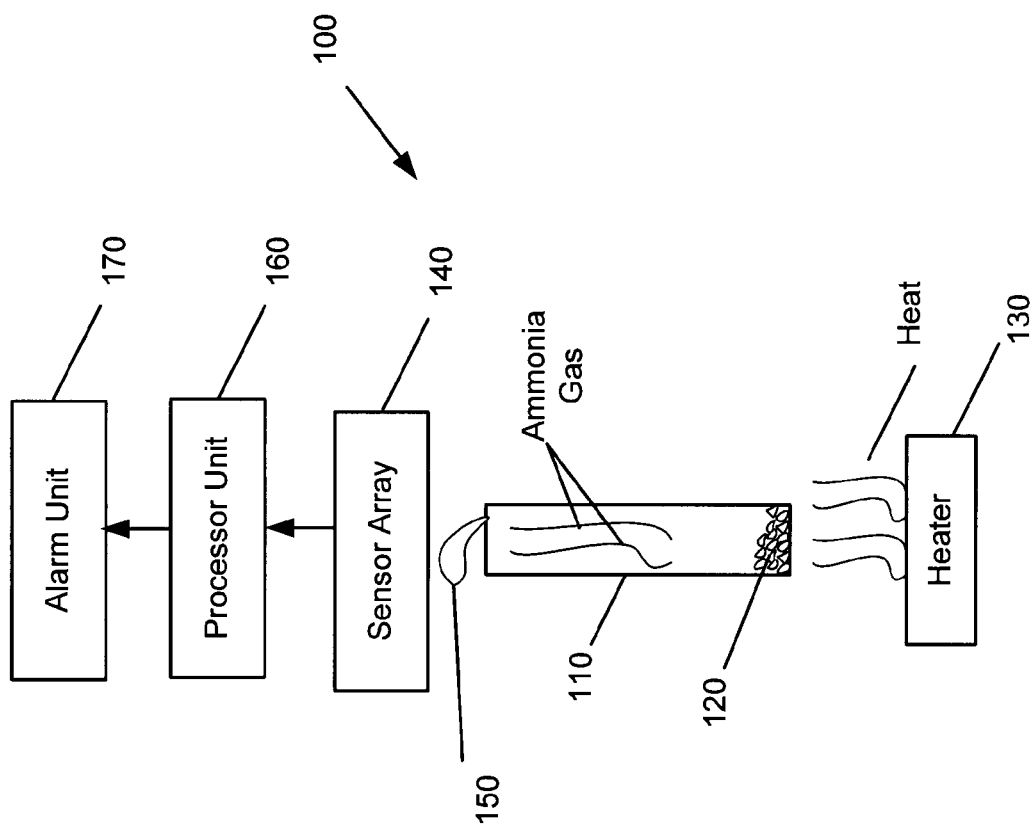
FIG. 1 is an IMS device according to an embodiment of the invention.

Reference will now be made in detail to embodiments, examples of which are illustrated in the accompanying drawings. An effort has been made to use the same reference numbers throughout the drawings to refer to the same or like parts.

Unless explicitly stated otherwise, "and" can mean "or," and "or" can mean "and." For example, if a feature is described as having A, B, or C, the feature can have A, B, and C, or any combination of A, B. and C. Similarly, if a feature is described as having A, B, and C, the feature can have only one or two of A, B, or C.

Unless explicitly stated otherwise, "a" and "an" can mean "one or more than one." For example, if a device is described as having a feature X, the device may have one or more of feature X.

The inventors of this application have found that calibrants and reactants used in conventional ion mobility spectrometry systems can impair the ability to detect species of interest by suppressing the signal amplitude of the species of interest or having coincident drift times, for example. This can be a particular problem with weakly ionized species, such as TATP (triacetone triperoxide).

TATP is an explosive that can be detected using an ion mobility spectrometer (IMS). When ionized in an IMS, TATP generates both positive and negative ions. Positive ions are weakly ionized and have a low proton affinity. Current calibrants and reactants in the positive mode either suppress the signal amplitude of TATP and other weakly ionized positive ions, or have coincident drift time peaks. Thus, these calibrants and reactants make detection of TATP more difficult or impossible.

In order for the IMS detector to have good sensitivity to the weakly ionized substances, the reactant/calibrant must not interfere with the ionization process or mask the ion's unique drift-time peaks.

The inventors of this application have found that ammonium sulfate and ammonium chloride have excellent properties for use as calibrants and/or reactants for ion mobility spectrometry. Ammonium sulfate, for example, produces appropriate characteristics of vapor pressure, ion peak drift time and amplitude, reactant capability, and proton affinity to permit use in a permeation tube when used in combination with an ion mobility spectrometer running in the positive mode.

In some embodiments, ammonium sulfate can be the ammonium salts used, as calibrants and reactants, and in other embodiments, ammonium chloride can be the ammonium salts used as calibrants and reactants. In other embodiments, ammonium chloride, or ammonium nitrate can be used as calibrants and reactants.

Ammonium sulfate can be preferable because it has the correct vapor pressure to permeate through Teflon-walled permeation tubes currently provided in IMS devices to provide a calibrating peak in the positive mode that the IMS detector can utilize. In addition, ammonium sulfate can release a suitable amount of ammonia without flood the detector with large amounts of toxic ammonia that must be vented. In addition, ammonium sulfate is a stable solid that can be easily handled. Ammonium sulfate provides a source of ammonium ions that lasts for a prolonged period of time on the order of months, and unlike ammonium hydroxide, it does not require special handling and does not melt when constant heat is applied from a calibrant heater. Ammonium carbamate, which is described for use in an IMS device in U.S. Patent Publication 2009/0166531,does not have such advantageous properties as described above with respect to ammonium sulfate.

In addition, unlike a previously tested calibrant/reactant candidate hydronium ion, the ammonium peak generated from ammonium sulfate was less susceptible to the presence of large quantities of water vapour, isopropyl alcohol, fingerprint contamination, and dirt contamination, which usually suppress the detector's ability to detect explosives in trace quantities.

In addition, unlike the hydronium calibrant/reactant, the calibrating peak of ammonium ions did not shift dramatically to longer drift time when the IMS detector was operated under a range of environmental conditions going from very dry to very humid conditions.

In some embodiments, the ammonium sulfate in solid form can be provided already packaged in a permeation tube. Any suitable permeation tube can be used to house the ammonium sulfate, including Teflon permeation tubes.

In some embodiments, the ammonium sulfate can be treated to enhance releasing ammonia to the system. In other embodiments, no treatment is used and ammonium sulfate produces ammonia without any special treatment or temperatures elevated above room temperature. Treatments can include but or not limited to, for example, heating, atmospheric pressure change, increased fluid flow, change in fluid type, and the like.

FIG. 1 shows an IMS device 100 according to an embodiment of the invention. The IMS device 100 includes a permeation tube 110, which contains ammonium sulfate 120 in solid form. The ammonium sulfate 120 is heated by a heater 130, and ammonia gas is created. The ammonia gas flows through the permeation tube 110 to an array of sensors 140, which are put in contact with or placed adjacent to an unknown sample 150. Detection signals provided by the array of sensors 140 are provided to a processor unit 160, which analyzes the spectral characteristics of the unknown sample 150 provided in the detection signals in order to attempt to identify the unknown sample 150. If the unknown sample 150 is determined to be an explosive or narcotic, for example, an alarm is generated by an alarm unit 170.

Ammonium sulfate can be used in a method of performing IMS. For example, the ammonium sulfate particles can be heated to release a sufficient amount of ammonia. In yet another embodiment, characteristics of the ammonia can be measured to calibrate the IMS.

Figure 2:
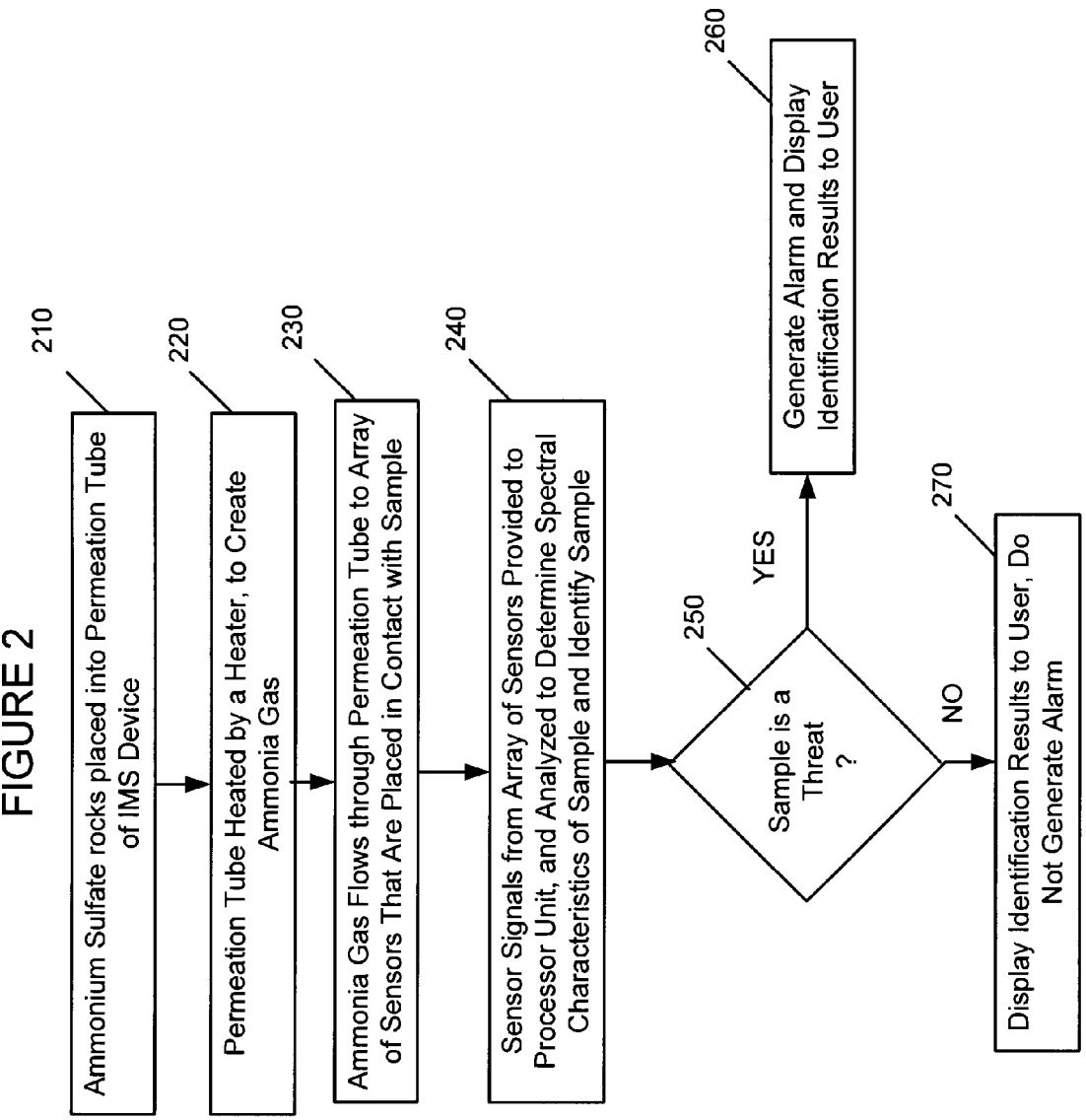
FIG. 2 is a flow chart of a method for providing a calibrant for an ion IMS device, according to an embodiment of the invention.

FIG. 2 shows a method for utilizing ammonium sulfate as a calibrant/reactant for an IMS device according to an embodiment of the invention. In a step 210, ammonium sulfate can be placed into a permeation tube of an IMS device. Each of the solid ammonium sulfate particles can be on the order of 5 to 50 mm in size, for example. In a step 220, the permeation tube with the ammonium sulfate particles disposed therewithin can be heated by a heater, to create ammonia gas. In a step 230, the ammonia gas flows through the permeation tube to an array of sensors of the IMS device, whereby the array of sensors can be placed in contact with or placed adjacent to an unknown sample. In a step 240, sensor signals output by the array of sensors are provided to a processor unit of the IMS device, and those signals are analyzed to determine spectral characteristics of the unknown sample and to thereby identify the unknown sample. If the unknown sample can be determined to be a "threat", such as a chemical or biological threat, in step 250, then an alarm can be generated in step 260. If the unknown sample is determined not to be a threat, then in step 270 no alarm is generated, and whereby information as to the identity of the unknown sample is provided to a user of the IMS device on a display of the IMS device, for example, or via a voice alert function of the IMS device (e.g., "The sample is liquid and is not a threat").

The embodiments described above are set forth herein for the purpose of illustration. This description, however, should not be deemed to be a limitation on the scope. Various modifications, adaptations, and alternatives may occur to one skilled in the art without departing from the claimed inventive concept. For example, heating is not the only option for releasing caibrant, whereby room temperature could be utilized to release calibrant with a device having very thin tubes. Accordingly, any suitable means can be employed in the present invention to release sufficient ammonia, e.g., proper combination of ambient temperature and permeation tube permeability. The spirit and scope of the invention are indicated, but not limited, by the following claims.

What is claimed is:

1. An ion mobility spectrometer, comprising:
   a permeation tube;
   ammonium sulfate disposed within the permeation tube in solid form; and a heating device configured to heat the permeation tube so as to create ammonia gas to flow within the permeation tube.

2. The ion mobility spectrometer according to claim 1, further comprising:
an array of sensors configured to receive the ammonia gas flowing out of one end of the permeation tube,
wherein the array of sensors is configured to provide detection signals when placed in contact with an unknown sample to be identified by the ion mobility spectrometer.

3. The ion mobility spectrometer according to claim 2, further comprising:
a processor unit configured to receive the detection signals output by the array of sensors, and to perform ion spectrometry analysis so as to identify the unknown sample.

4. A method of calibrating an ion mobility spectrometer, comprising:
heating a permeation tube containing at least ammonium sulfate disposed within the permeation tube in solid form, to thereby release ammonia; and
detecting the ammonia.

5. The method according to claim 4, wherein the detecting is performed on the ammonia in gaseous form.

6. The method according to claim 4, further comprising:
placing an array of sensors of the ion mobility spectrometer in contact with an unknown sample at a same time the ammonia is provided to the array of sensors; and
providing detection signals from the array of sensors to a processing unit, in order to identify the unknown sample.

* * * * *